(12) United States Patent
Bressler et al.

(10) Patent No.: US 8,377,093 B2
(45) Date of Patent: Feb. 19, 2013

(54) METHOD OF REMOVING A VEIN FILTER

(75) Inventors: James Erich Bressler, Langhorne, PA (US); David M. Schaller, Wallingford, PA (US); James F. McGuckin, Jr., Radnor, PA (US)

(73) Assignee: Rex Medical, L.P., Conshohocken, PA (US)

(*) Notice: Subject to any disclaimer, the term of this patent is extended or adjusted under 35 U.S.C. 154(b) by 0 days.

(21) Appl. No.: 13/172,355

(22) Filed: Jun. 29, 2011

(65) Prior Publication Data

US 2011/0313444 A1  Dec. 22, 2011

Related U.S. Application Data (60) Division of application No. 11/801,547, filed on May 10, 2007, now Pat. No. 7,976,562, and a continuation-in-part of application No. 10/889,429, filed on Jul. 12, 2004, now Pat. No. 7,704,266, and a continuation-in-part of application No. 10/805,796, (Continued)

(51) Int. Cl.
*A61F 2/01* (2006.01)
*A61F 2/84* (2006.01)

(52) U.S. Cl. ........... 606/200; 623/1.11

(58) Field of Classification Search ......... 606/108, 606/194, 200; 623/1.11, 1.12; 604/525, 604/528, 532; 600/585

See application file for complete search history.

(56) References Cited

U.S. PATENT DOCUMENTS

| 3,744,492 A | 7/1973 | Leibinsohn |
| 3,952,747 A | 4/1976 | Kimmell, Jr. |
| 4,266,815 A | 5/1981 | Cross |
| 4,425,908 A | 1/1984 | Simon |
| 4,494,531 A | 1/1985 | Gianturco |
| 4,512,338 A | 4/1985 | Balko et al. |
| 4,619,246 A | 10/1986 | Molgaard-Nielsen et al. |
| 4,643,184 A | 2/1987 | Mobin-Uddin |
| 4,688,553 A | 8/1987 | Metals |
| 4,727,873 A | 3/1988 | Mobin-Uddin |
| 4,781,177 A | 11/1988 | Lebigot |
| 4,793,348 A | 12/1988 | Palmaz |
| 4,817,600 A | 4/1989 | Herms et al. |
| 4,832,055 A | 5/1989 | Palestrant |
| 4,957,501 A | 9/1990 | Lahille et al. |

(Continued)

FOREIGN PATENT DOCUMENTS

| DE | 3429850 | 2/1986 |
| WO | WO-9312723 | 7/1993 |

(Continued)

OTHER PUBLICATIONS

B. Braun Medical, Inc. Vena Tech ™ Vena Cava Filters, Feb. 2000.

(Continued)

*Primary Examiner* — Kathleen Sonnett
(74) *Attorney, Agent, or Firm* — Neil D. Gershon (57) ABSTRACT

A method of removing an implanted vessel filter by a femoral approach comprising the steps of providing a catheter, inserting a curved device into the catheter to a position proximal of the tip, advancing the catheter tip through the femoral vein and past a cranial end of the filter, inserting the curved device into the catheter tip to move the catheter tip to a more curved position, and inserting a filter grasping device though the curved device and catheter tip to exit a distal portion to grasp the filter.

8 Claims, 11 Drawing Sheets

Related U.S. Application Data filed on Mar. 22, 2004, now Pat. No. 7,338,512.

(60) Provisional application No. 60/818,202, filed on Jun. 30, 2006, provisional application No. 60/572,274, filed on May 18, 2004, provisional application No. 60/538,379, filed on Jan. 22, 2004.

(56) References Cited

U.S. PATENT DOCUMENTS

| | | |
|---|---|---|
| 4,983,169 A | 1/1991 | Furukama |
| 4,990,156 A | 2/1991 | Lefebvre |
| 4,994,069 A | 2/1991 | Ritchart et al. |
| 5,059,205 A | 10/1991 | El-Nounou et al. |
| 5,133,733 A | 7/1992 | Rasmussen et al. |
| 5,152,777 A | 10/1992 | Goldberg et al. |
| 5,231,989 A | 8/1993 | Middleman |
| 5,234,458 A | 8/1993 | Metais |
| 5,300,086 A | 4/1994 | Gory et al. |
| 5,324,304 A | 6/1994 | Rasmussen |
| 5,344,427 A | 9/1994 | Cottenceau et al. |
| 5,345,937 A | 9/1994 | Middleman |
| 5,350,398 A | 9/1994 | Pavcnik et al. |
| 5,370,657 A | 12/1994 | Irie |
| 5,375,612 A | 12/1994 | Cottenceau et al. |
| 5,382,261 A | 1/1995 | Palmaz |
| 5,383,887 A | 1/1995 | Nadal |
| 5,405,377 A | 4/1995 | Cragg |
| 5,531,788 A | 7/1996 | Dibie et al. |
| 5,591,197 A | 1/1997 | Orth et al. |
| 5,601,595 A | 2/1997 | Smith |
| 5,626,605 A | 5/1997 | Irie et al. |
| 5,630,801 A | 5/1997 | Roussigne et al. |
| 5,634,942 A | 6/1997 | Chevillon et al. |
| 5,681,347 A | 10/1997 | Catheart et al. |
| 5,683,411 A | 11/1997 | Kavteladze et al. |
| 5,690,671 A | 11/1997 | McGurk et al. |
| 5,709,704 A | 1/1998 | Nott et al. |
| 5,725,552 A | 3/1998 | Kotula et al. |
| 5,733,294 A | 3/1998 | Forber et al. |
| 5,733,329 A | 3/1998 | Wallace et al. |
| 5,746,767 A | 5/1998 | Smith |
| 5,755,779 A | 5/1998 | Horiguchi |
| 5,755,790 A | 5/1998 | Chevillon et al. |
| 5,776,162 A | 7/1998 | Kleshinski |
| 5,782,748 A | 7/1998 | Palmer et al. |
| 5,795,322 A | 8/1998 | Boudewijn |
| 5,810,874 A | 9/1998 | Lefebvre |
| 5,836,968 A | 11/1998 | Simon et al. |
| 5,853,420 A | 12/1998 | Chevillon et al. |
| 5,893,869 A | 4/1999 | Barnhart et al. |
| 5,895,398 A | 4/1999 | Wensel et al. |
| 5,895,410 A | 4/1999 | Forber et al. |
| 5,911,717 A | 6/1999 | Jacobsen et al. |
| 5,968,071 A | 10/1999 | Chevillon et al. |
| 5,976,172 A | 11/1999 | Homsma et al. |
| 5,984,947 A | 11/1999 | Smith |
| 6,007,558 A | 12/1999 | Ravenscroft et al. |
| 6,011,988 A | 1/2000 | Lynch |
| 6,013,093 A | 1/2000 | Nott et al. |
| 6,042,598 A | 3/2000 | Tsugita et al. |
| 6,059,825 A | 5/2000 | Hobbs et al. |
| 6,063,113 A | 5/2000 | Kavteladze et al. |
| 6,066,158 A | 5/2000 | Engelson et al. |
| 6,074,361 A | 6/2000 | Jacobs |
| 6,080,178 A | 6/2000 | Meglin |
| 6,093,196 A | 7/2000 | Okada |
| 6,093,199 A | 7/2000 | Brown et al. |
| 6,096,052 A | 8/2000 | Callister et al. |
| 6,096,196 A | 8/2000 | Okada |
| 6,099,549 A | 8/2000 | Bosma et al. |
| 6,117,154 A | 9/2000 | Barbut et al. |
| 6,123,715 A | 9/2000 | Amplatza |
| 6,126,673 A | 10/2000 | Kim et al. |
| 6,146,404 A | 11/2000 | Kim et al. |
| 6,152,946 A | 11/2000 | Broome et al. |
| 6,165,179 A | 12/2000 | Cathcart et al. |
| 6,165,198 A | 12/2000 | McGurk et al. |
| 6,168,579 B1 | 1/2001 | Tsugita |
| 6,168,603 B1 | 1/2001 | Leslie et al. |
| 6,171,327 B1 | 1/2001 | Daniel et al. |
| 6,171,328 B1 | 1/2001 | Addis |
| 6,179,851 B1 | 1/2001 | Barbut et al. |
| 6,179,859 B1 | 1/2001 | Bates et al. |
| 6,187,025 B1 | 2/2001 | Machek |
| 6,193,739 B1 | 2/2001 | Chevillon et al. |
| 6,214,025 B1 | 4/2001 | Thistle et al. |
| 6,217,600 B1 | 4/2001 | DiMatteo |
| 6,231,581 B1 | 5/2001 | Shank et al. |
| 6,231,589 B1 | 5/2001 | Wessman et al. |
| 6,235,000 B1 | 5/2001 | Milo |
| 6,235,044 B1 | 5/2001 | Root et al. |
| 6,235,045 B1 | 5/2001 | Barbut et al. |
| 6,241,746 B1 | 6/2001 | Bosma et al. |
| 6,245,012 B1 | 6/2001 | Kleshinski et al. |
| 6,251,122 B1 | 6/2001 | Tsukernik |
| 6,258,026 B1 | 7/2001 | Ravenscroft et al. |
| 6,267,776 B1 | 7/2001 | O'Connell |
| 6,273,901 B1 | 8/2001 | Whitcher et al. |
| 6,280,451 B1 | 8/2001 | Bates et al. |
| 6,280,457 B1 | 8/2001 | Wallace et al. |
| 6,290,721 B1 | 9/2001 | Heath |
| 6,328,755 B1 | 12/2001 | Marshall |
| 6,331,183 B1 | 12/2001 | Suon |
| 6,331,184 B1 | 12/2001 | Abrams |
| 6,342,062 B1 | 1/2002 | Suon et al. |
| 6,342,063 B1 | 1/2002 | Devries et al. |
| 6,344,041 B1 | 2/2002 | Kupiecki et al. |
| 6,355,051 B1 | 3/2002 | Sisskind et al. |
| 6,368,338 B1 | 4/2002 | Konya et al. |
| 6,383,205 B1 | 5/2002 | Samson et al. |
| 6,402,771 B1 | 6/2002 | Palmer et al. |
| 6,436,120 B1 | 8/2002 | Meglin |
| 6,436,121 B1 | 8/2002 | Blom |
| 6,443,971 B1 | 9/2002 | Boylan et al. |
| 6,443,972 B1 | 9/2002 | Bosma et al. |
| 6,447,522 B2 | 9/2002 | Gambale |
| 6,447,530 B1 | 9/2002 | Ostrovsky et al. |
| 6,447,531 B1 | 9/2002 | Amplatz |
| 6,458,139 B1 | 10/2002 | Palmer et al. |
| 6,468,290 B1 | 10/2002 | Weldon et al. |
| 6,482,222 B1 | 11/2002 | Bruckheimer et al. |
| 6,506,205 B2 | 1/2003 | Goldberg et al. |
| 6,517,559 B1 | 2/2003 | O'Connell |
| 6,527,962 B1 | 3/2003 | Nadal |
| 6,537,294 B1 | 3/2003 | Boyle et al. |
| 6,540,767 B1 | 4/2003 | Walak et al. |
| 6,551,342 B1 | 4/2003 | Shen et al. |
| 6,562,058 B2 | 5/2003 | Sequin et al. |
| 6,572,593 B1 | 6/2003 | Duam |
| 6,592,559 B1 | 7/2003 | Pakter |
| 6,599,307 B1 | 7/2003 | Huter et al. |
| 6,605,102 B1 | 8/2003 | Mazzocchi et al. |
| 6,632,184 B1 | 10/2003 | Truwit |
| 6,652,558 B2 | 11/2003 | Patel et al. |
| 6,656,202 B2 | 12/2003 | Papp et al. |
| 6,660,021 B1 | 12/2003 | Palmer et al. |
| 6,695,878 B2 | 2/2004 | McGuckin et al. |
| 6,783,538 B2 | 8/2004 | McGuckin et al. |
| 6,793,665 B2 | 9/2004 | McGuckin et al. |
| 6,890,340 B2 | 5/2005 | Duane |
| 6,932,831 B2 | 8/2005 | Forber |
| 6,958,074 B2 | 10/2005 | Russell |
| 6,966,914 B2 | 11/2005 | Abe |
| 6,972,025 B2 | 12/2005 | WasDyke |
| 6,989,021 B2 | 1/2006 | Bosma et al. |
| 6,994,092 B2 | 2/2006 | va der Burg et al. |
| 7,037,321 B2 | 5/2006 | Sachdeva et al. |
| 7,097,651 B2 | 8/2006 | Harrison et al. |
| 7,232,462 B2 | 6/2007 | Schaeffer et al. |
| 7,279,000 B2 | 10/2007 | Cartier et al. |
| 7,316,708 B2 | 1/2008 | Gordon et al. |
| 7,534,251 B2 | 5/2009 | WasDyke et al. |
| 7,572,289 B2 | 8/2009 | Sisken et al. |
| 7,625,390 B2 | 12/2009 | Hendriksen et al. |

| | | | |
|---|---|---|---|
| 7,704,266 B2 | 4/2010 | Thinnes et al. | |
| 7,867,245 B2 | 1/2011 | Neeman et al. | |
| 7,875,018 B2* | 1/2011 | Tockman et al. | 604/510 |
| 2002/0058911 A1 | 5/2002 | Gilson et al. | |
| 2002/0116024 A1 | 8/2002 | Goldberg et al. | |
| 2002/0193827 A1 | 12/2002 | McGuckin et al. | |
| 2002/0193828 A1 | 12/2002 | Griffin et al. | |
| 2003/0130680 A1 | 7/2003 | Russell | |
| 2003/0195555 A1 | 10/2003 | Khairkhahan et al. | |
| 2003/0208227 A1 | 11/2003 | Thomas | |
| 2003/0208253 A1 | 11/2003 | Beyer et al. | |
| 2004/0044361 A1 | 3/2004 | Frazier et al. | |
| 2004/0073252 A1 | 4/2004 | Goldberg et al. | |
| 2004/0093017 A1 | 5/2004 | Chanduszko | |
| 2004/0158273 A1 | 8/2004 | Weaver et al. | |
| 2004/0186510 A1 | 9/2004 | Weaver | |
| 2004/0215230 A1 | 10/2004 | Frazier et al. | |
| 2004/0230220 A1 | 11/2004 | Osborne | |
| 2005/0004596 A1 | 1/2005 | McGuckin et al. | |
| 2005/0015111 A1 | 1/2005 | McGuckin et al. | |
| 2005/0043757 A1 | 2/2005 | Arad et al. | |
| 2005/0165442 A1 | 7/2005 | Thinnes et al. | |
| 2005/0182439 A1 | 8/2005 | Lowe | |
| 2005/0234503 A1 | 10/2005 | Ravenscroft et al. | |
| 2005/0251199 A1 | 11/2005 | Osborne et al. | |
| 2005/0267512 A1 | 12/2005 | Osborne et al. | |
| 2005/0267514 A1 | 12/2005 | Osborne et al. | |
| 2005/0288704 A1 | 12/2005 | Cartier et al. | |
| 2006/0030875 A1 | 2/2006 | Tessmer | |
| 2006/0058832 A1 | 3/2006 | Melzer et al. | |
| 2006/0079928 A1 | 4/2006 | Cartier et al. | |
| 2006/0079930 A1 | 4/2006 | McGuckin, Jr. et al. | |
| 2006/0100660 A1 | 5/2006 | Osborne et al. | |
| 2006/0106417 A1 | 5/2006 | Tessmer et al. | |
| 2006/0149295 A1* | 7/2006 | Fleming, III | 606/113 |
| 2006/0178695 A1 | 8/2006 | Decant et al. | |
| 2006/0206138 A1 | 9/2006 | Eidenschink | |
| 2007/0005095 A1 | 1/2007 | Osborne et al. | |
| 2007/0032816 A1 | 2/2007 | O'Connell et al. | |
| 2007/0088381 A1 | 4/2007 | McGuckin, Jr. et al. | |
| 2007/0167974 A1 | 7/2007 | Cully et al. | |
| 2007/0173885 A1 | 7/2007 | Cartier et al. | |
| 2007/0198050 A1 | 8/2007 | Ravenscroft et al. | |
| 2008/0188887 A1 | 8/2008 | Batiste | |
| 2008/0221609 A1 | 9/2008 | McGuckin et al. | |
| 2008/0275486 A1 | 11/2008 | Dwyer et al. | |
| 2009/0198270 A1 | 8/2009 | McGuckin et al. | |
| 2010/0049239 A1 | 2/2010 | McGuckin et al. | |

FOREIGN PATENT DOCUMENTS

| | | |
|---|---|---|
| WO | WO-9509567 | 4/1995 |
| WO | WO-9925252 | 5/1999 |
| WO | WO-0110342 | 2/2001 |
| WO | WO-0145590 | 6/2001 |
| WO | WO-0162184 | 8/2001 |
| WO | WO-0172239 | 10/2001 |
| WO | 0211812 | 2/2002 |
| WO | WO-02/102436 | 12/2002 |
| WO | WO-03063732 | 8/2003 |
| WO | WO-2004049973 | 6/2004 |
| WO | 2005/117750 | 12/2005 |
| WO | 2006/036457 | 4/2006 |

OTHER PUBLICATIONS

Gianturco-Roehm, Bird's Nest® Vena Cava Filter.

Cordis Corporation, TrapEase™ Permanent Vena Cava Filter. "A Small, Easy and Versatile System for Optimal Pulmonary Emboli Prevention", 2000 (4 pages).

* cited by examiner

FIG_3

FIG_4

FIG_5

FIG_8

FIG_9

FIG_10

FIG_11

FIG_11A

FIG_12

FIG_13

FIG_14

FIG_15A

FIG_15B

FIG_16

FIG_18

FIG_19

METHOD OF REMOVING A VEIN FILTER

This application is a divisional of application Ser. No. 11/801,547, filed May 10, 2007, now U.S. Pat. No. 7,976,562, which claims priority from provisional application Ser. No. 60/818,202, filed Jun. 30, 2006, and is a continuation-in-part of application Ser. No. 10/889,429, filed Jul. 12, 2004, now U.S. Pat. No. 7,704,266, which claims priority from provisional application Ser. No. 60/572,274, filed May 18, 2004 and is a continuation-in-part of application Ser. No. 10/805,796, filed Mar. 22, 2004, now U.S. Pat. No. 7,338,512, which claims priority from provisional application Ser. No. 60/538,379, filed Jan. 22, 2004. The entire contents of each of these applications are incorporated herein by reference.

BACKGROUND

1. Technical Field

This application relates to a vascular filter and more particularly to a method of removing a vein filter from the vessel.

2. Background of Related Art

Passage of blood clots to the lungs is known as pulmonary embolism. These clots typically originate in the veins of the lower limbs and can migrate through the vascular system to the lungs where they can obstruct blood flow and therefore interfere with oxygenation of the blood. Pulmonary embolisms can also cause shock and even death.

In some instances, blood thinning medication, e.g. anticoagulants such as Heparin, or sodium warfarin can be given to the patient. These medications, however, have limited use since they may not be able to be administered to patients after surgery or stroke or given to patients with high risk of internal bleeding. Also, this medication approach is not always effective in preventing recurring blood clots.

To avoid invasive surgery, less invasive surgical techniques involving placement of a mechanical barrier in the inferior vena cava have been developed. These barriers are in the form of filters and are typically inserted through either the femoral vein in the patient's leg or the right jugular vein in the patient's neck or arm under local anesthesia. The filters are then advanced intravascularly to the inferior vena cava where they are expanded to block migration of the blood clots from the lower portion of the body to the heart and lungs.

These prior filters take various forms. One type of filter is composed of coiled wires such as disclosed in U.S. Pat. Nos. 5,893,869 and 6,059,825. Another type of filter consists of legs with free ends having anchors for embedding in the vessel wall to hold the filter. These filters are disclosed, for example, in U.S. Pat. Nos. 4,688,553, 4,781,173, 4,832,055, and 5,059,205, 5,984,947 and 6,007,558. Another type of filter is disclosed in U.S. Pat. No. 6,214,025 consisting of wires twisted together to form a cylindrical anchoring portion conforming to the inner vessel wall surface to exert a radial force and a conical filtering portion.

Co-pending commonly assigned U.S. application Ser. No. 10/889,429 (the "'429 application"), the entire contents of which is incorporated herein by reference, discloses other forms of vein filters. These filters can be permanently implanted or removed minimally invasively, e.g. intravascularly. The '429 application discloses various configurations of the cranial end of the filter to facilitate removal. The filters of the '429 application are generally designed to be removed from a jugular approach since the retrieval hook portion is located on the cranial end. It would be advantageous to provide a method for retrieving these filters utilizing a femoral approach as well. Such femoral approach could advantageously also be utilized to retrieve other filters.

SUMMARY

The present invention provides a method of removing an implanted vessel filter by a femoral approach comprising the steps of: providing a catheter with a curved tip; inserting a straightening device into the catheter to move the catheter tip from a curved position to a more straightened position; advancing the catheter tip through the femoral vein and past a cranial end of the implanted filter; withdrawing the straightening device to enable the catheter tip to return to the curved position; and inserting a filter grasping device through the catheter and curved catheter tip to exit a distal portion to grasp the filter.

The step of inserting the filter grasping device preferably includes the step of inserting a snare to engage a hook portion at the cranial end of the filter. Preferably the method includes the step of pulling the filter into a lumen of the catheter after grasping of the filter. The step of advancing the catheter tip preferably includes the step of advancing the catheter and straightening device over a guidewire. Subsequent to the step of withdrawing the filter, the catheter tip is preferably moved to a more straightened position to facilitate removal of the catheter. The method steps may also include advancing the catheter after grasping the filter to disengage filter hooks from the vessel wall.

The present invention also provides a method of removing an implanted vessel filter by a femoral approach comprising the steps of providing a catheter with a tip; inserting a curved device into the catheter to a position proximal of the tip; advancing the catheter tip through the femoral vein and past a cranial end of the implanted filter; inserting the curved device into the catheter tip to move the catheter tip from a first more straightened position to a second more curved position; and inserting a filter grasping device though the curved device, catheter and curved catheter tip to exit a distal portion to grasp the filter.

The step of inserting the filter grasping device may include the step of inserting a snare to engage the filter. The catheter may have a first hardness at an intermediate portion and a second hardness less than the first hardness at the tip such that in the step of inserting the curved device, the first hardness maintains the curved device in a more straightened position and the second hardness allows the curved device to move to a more curved position to thereby move the catheter tip to the more curved position.

The method may further include the step of pulling the filter into a lumen of the curved device after grasping of the filter.

The method may further comprise the step of withdrawing the filter and grasping device through the catheter, wherein subsequent to the step of withdrawing the filter, the method includes the step of withdrawing the curved device from the catheter tip to move the catheter tip to a more straightened position.

BRIEF DESCRIPTION OF THE DRAWINGS

Preferred embodiment(s) of the present disclosure are described herein with reference to the drawings wherein:

FIGS. 3-14 illustrate the method steps of the present invention for retrieving a filter by a femoral approach, wherein

DETAILED DESCRIPTION OF PREFERRED EMBODIMENTS

Turning now to the drawings, wherein like reference numerals identify similar or like components throughout the several views, a method for retrieving vein filters utilizing a femoral approach is described. In co-pending commonly assigned patent application Ser. No. 10/889,429, filed Jul. 12, 2004, various embodiments of filters are described with various structures, e.g. hooks, to facilitate removal. The '429 application also describes retrieval of the filter through the catheter. Being that the retrieval structure of the filters is at the cranial end, the method of the present invention provides a way to retrieve those filters from the inferior vena cava, as well as other filters with retrieval hook or structure on the cranial end, utilizing a femoral approach.

Figures 1, 2:
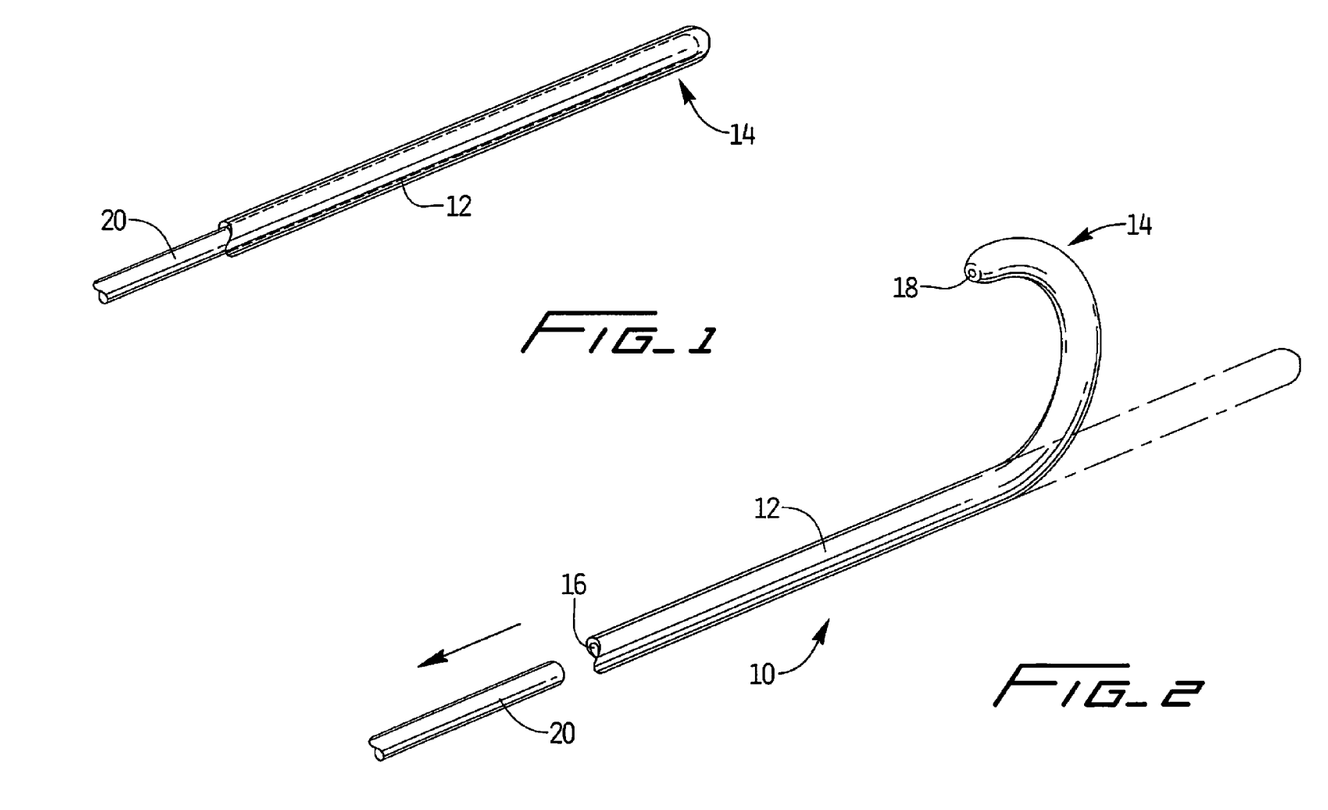
FIG. 1 is a broken perspective view of the retrieval catheter with a dilator positioned therein to straighten the catheter tip.
FIG. 2 is a broken perspective view of the catheter of FIG. 1 with the dilator removed and the catheter tip in the curved position.
Figure 3:
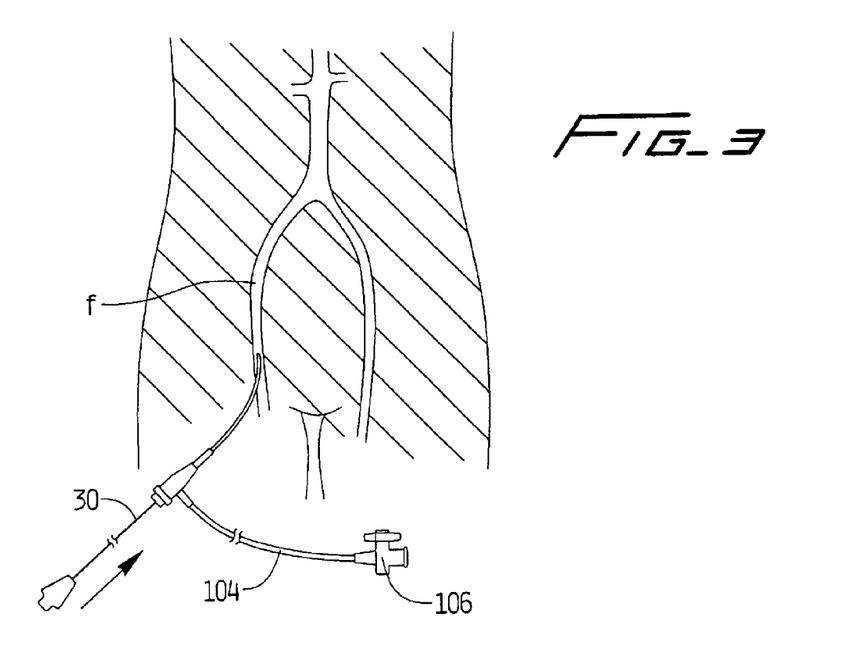
FIG. 3 illustrates initial insertion of the guidewire through the femoral vein.
Figure 4:
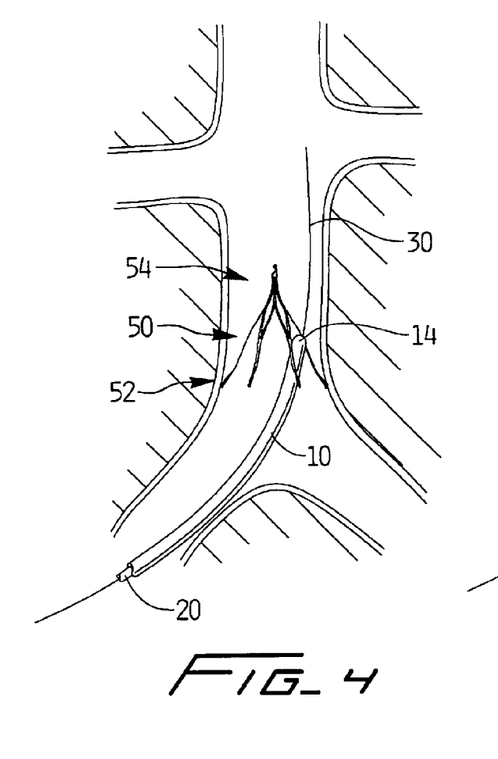
FIG. 4 illustrates the retrieval catheter being advanced over a guidewire toward the inferior vena cava just below (upstream) the juncture of the renal arteries to where the filter has been implanted.

Turning initially to FIG. 1, the retrieval catheter or sheath 10 of the present invention has a body 12 and a distal tip 14. The distal tip 14 has a curved shape as shown in FIG. 2 (the straightened shape is shown in phantom). The curved shape is the normal condition of the catheter tip 14 and the curve shown is about 180 degree turn although other curves are also contemplated. The curved catheter tip 14 is sufficiently flexible to be straightened by insertion of dilator 20 through lumen 16 as shown in FIG. 1.

Figure 5:
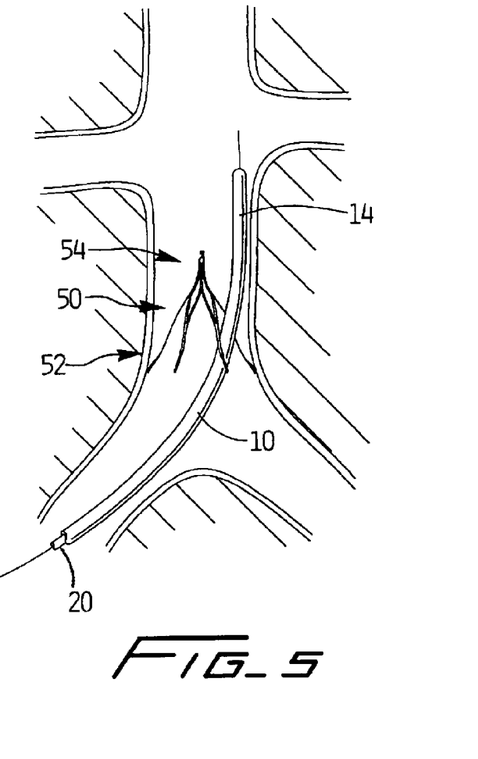
FIG. 5 illustrates the tip of the retrieval catheter being advanced beyond the implanted filter with the dilator still positioned in the catheter to maintain the catheter tip in the straightened position.

The retrieval method is illustrated by the method steps of FIGS. 3-14. After insertion of the guidewire 30 through the right femoral vein "f" (or alternatively the left), the guidewire 30 is maneuvered past the cranial end 54 of filter 50. Retrieval catheter 10, with dilator 20 positioned therein, is then inserted through the femoral vein "f" and advanced through the iliac veins into the inferior vena cava. (Tubing 104 and valve assembly 106 enable saline injection described below.) That is, dilator 20 is positioned in the lumen 16 of the retrieval catheter 10 during insertion to move and maintain the tip 14 in the substantially straightened position (or more straightened position) to enable advancement of the catheter through the vascular system. Retrieval catheter 10 and dilator 20 are inserted over guidewire 30 past the caudal end 52 of the filter 50 and beyond the cranial end 54 as shown in FIG. 5.

Figure 6:
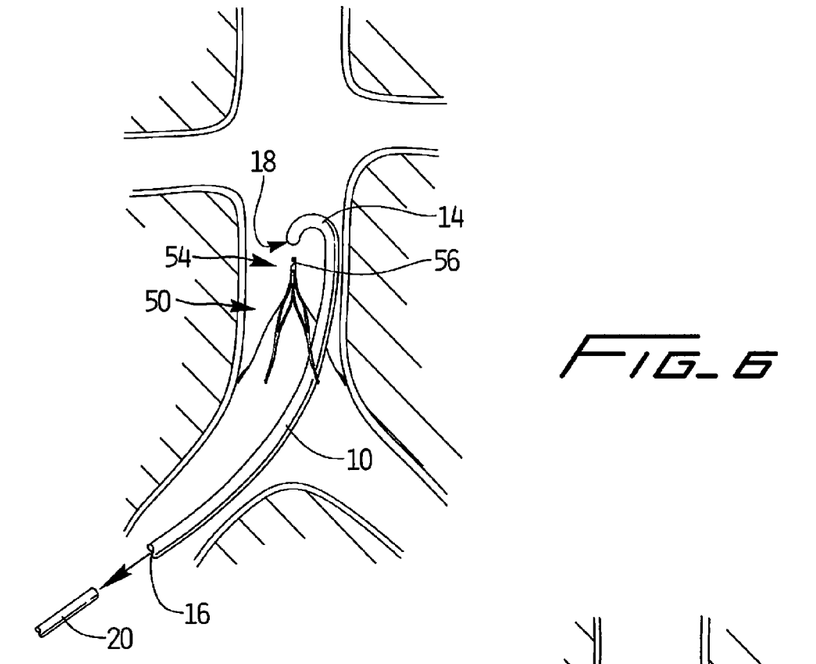
FIG. 6 illustrates the dilator being withdrawn to enable the catheter tip to return to its normally curved position.

Dilator 20 (and guidewire 30) is then withdrawn as shown by the arrow in FIG. 6, which enables the distal tip 14 of catheter 10 to return to its normal more curved configuration. In this curved configuration, the distal opening 18 of catheter 10 faces the cranial end of the filter and is maneuvered so opening 18 is above the hook 56 of filter 50. It could also be placed to substantially align with the hook.

Figure 7:
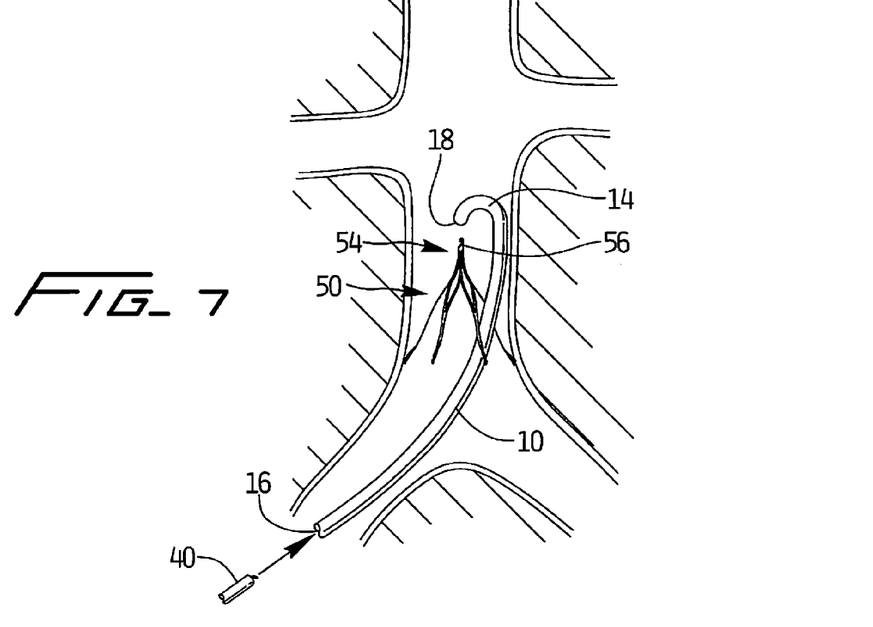
FIG. 7 illustrates a filter retrieval snare being inserted into the retrieval catheter.
Figures 8, 9:
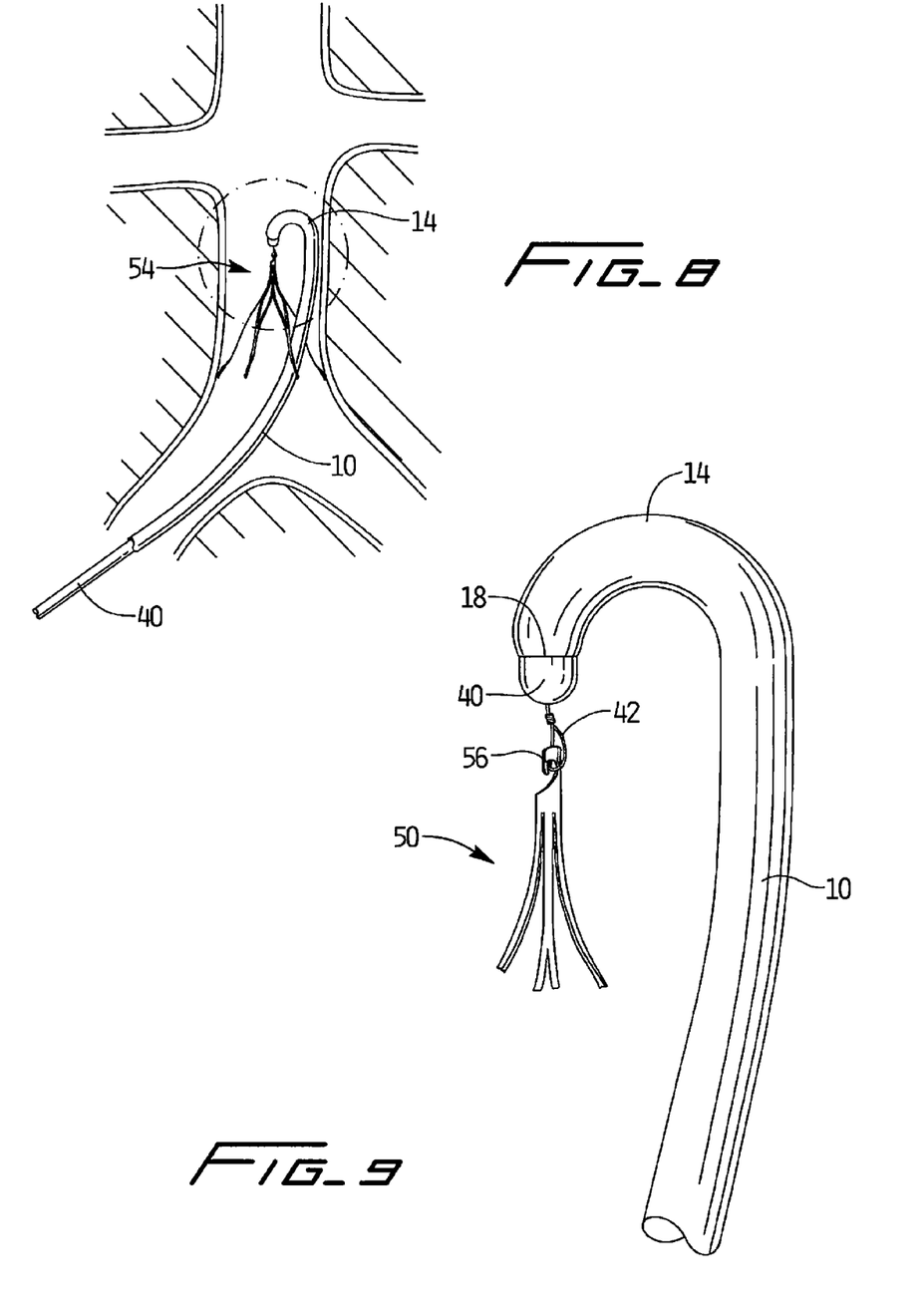
FIG. 8 illustrates the filter retrieval snare advanced through the retrieval catheter, the snare shown exiting the distal tip of the catheter and engaging the cranial end of the filter.
FIG. 9 is a close up view of the area of detail of FIG. 8 showing the snare engaging the retrieval hook at the cranial end of the filter.

Snare catheter 40 is inserted through the lumen 16 of the retrieval catheter 10, as shown by the arrow of FIG. 7, and extends around the curved distal tip 14 of catheter 10 as shown in FIGS. 8 and 9, exiting distal opening 18.

Figures 10, 11:
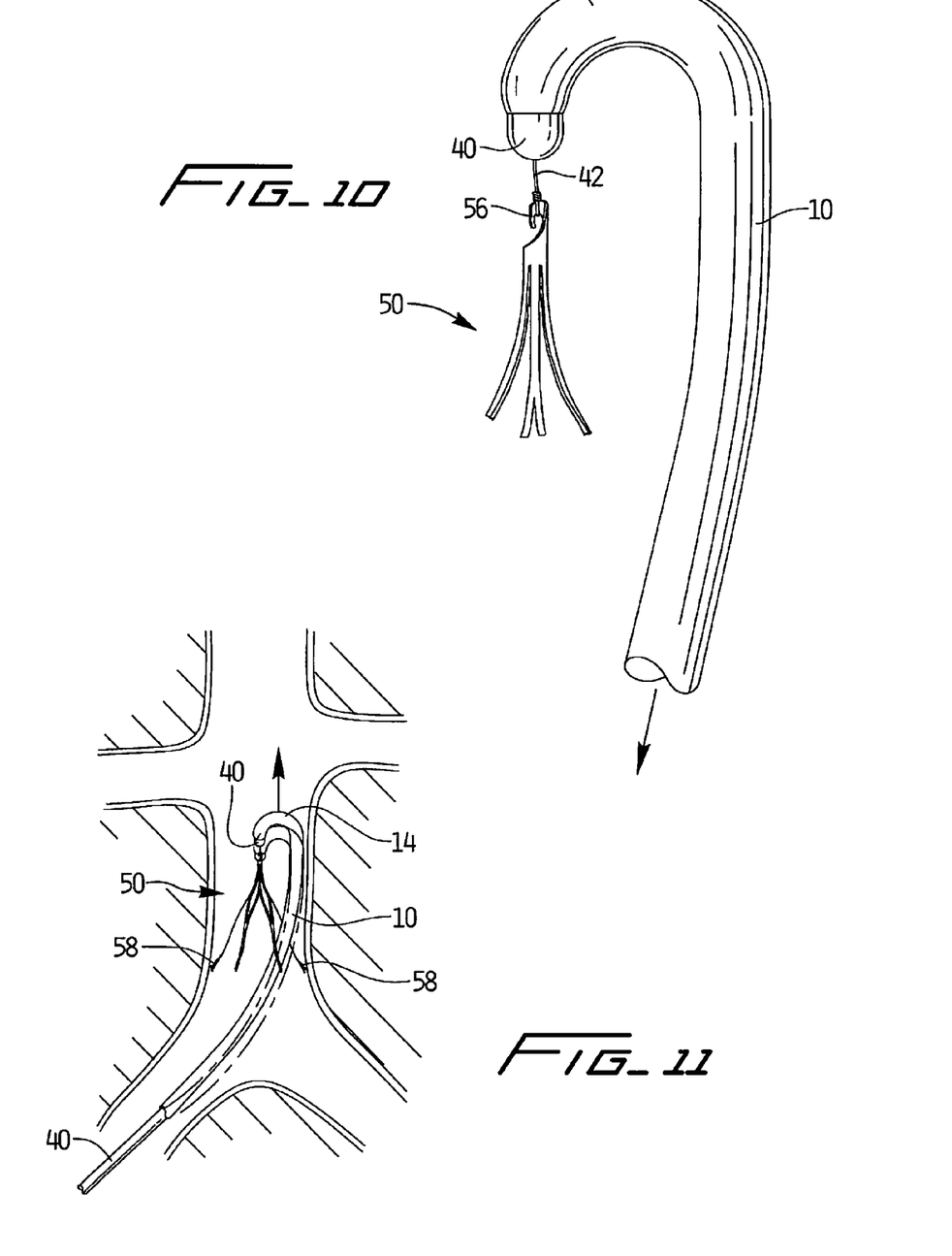
FIG. 10 is a close up view similar to FIG. 9 except showing the snare tightened around the retrieval hook of the filter.
FIG. 11 illustrates movement of the retrieval catheter distally to disengage the filter retention hooks from the vessel wall.
Figure 11A:
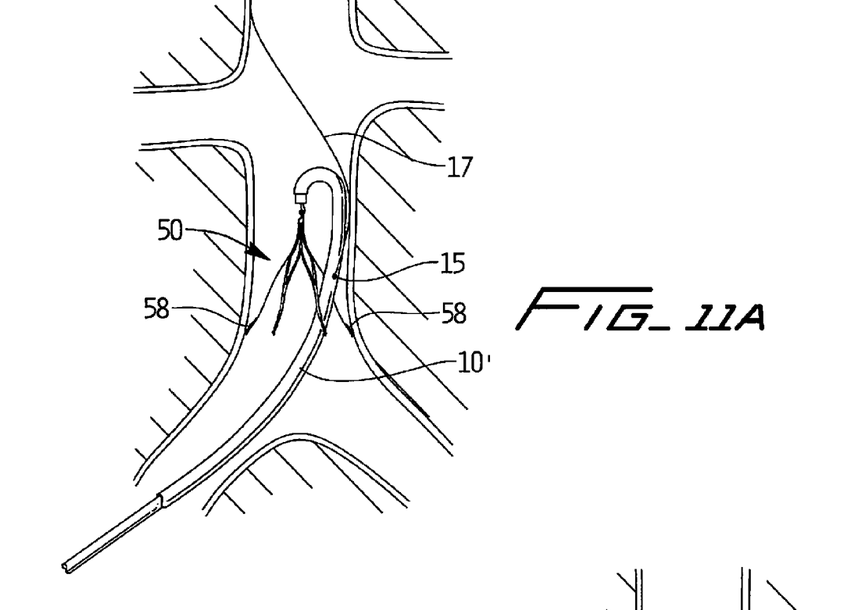
FIG. 11A illustrates an alternate embodiment to aid movement of the retrieval catheter distally by the use of a wire.

The snare 42, movably positioned in a lumen of the snare catheter 40, is placed around hook 56 of filter 50, and then tightened around the hook as shown in FIG. 10, by retraction of the snare wire to grasp the filter. Once tightened, the catheter 10 is preferably moved distally (shown in phantom) in the direction of the arrow of FIG. 11 to disengage the filter retention hooks 58 from the vessel wall. To facilitate such distal advancement and hook disengagement, a wire can be used as shown in the alternate embodiment of FIG. 11A. In this embodiment, catheter 10' has a side opening 15 through which wire 17 extends from the catheter lumen, either the lumen for the snare or another lumen adjacent to the snare lumen. This stiffening wire 17 is pushed forward along with the retrieval catheter 10' to help move the catheter distally by providing additional force on the catheter.

Figure 12:
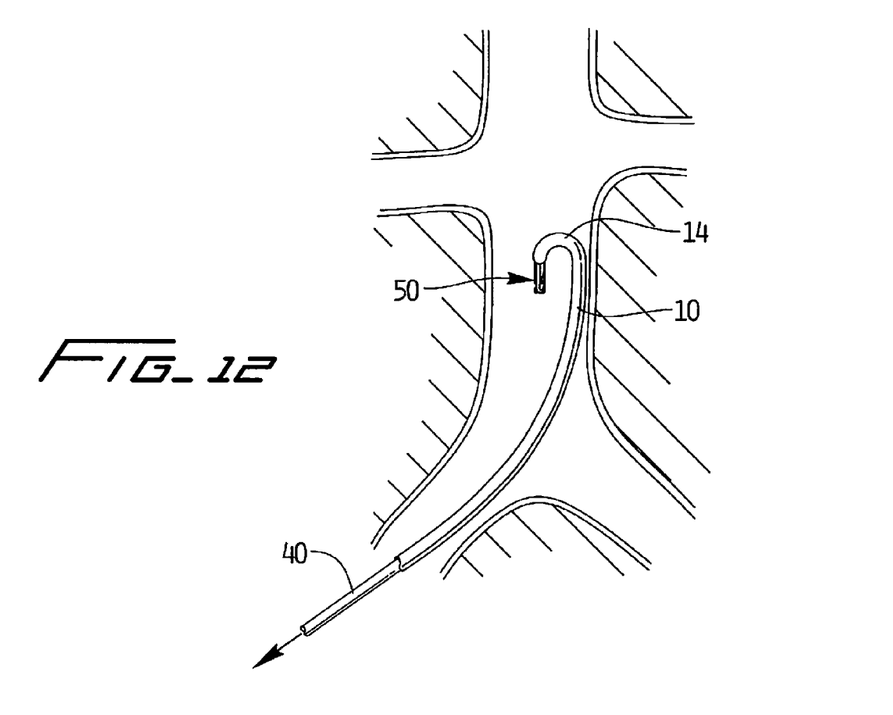
FIG. 12 illustrates retraction of the retrieval snare to remove the filter from the vessel and pull it through the retrieval catheter.
Figure 13:
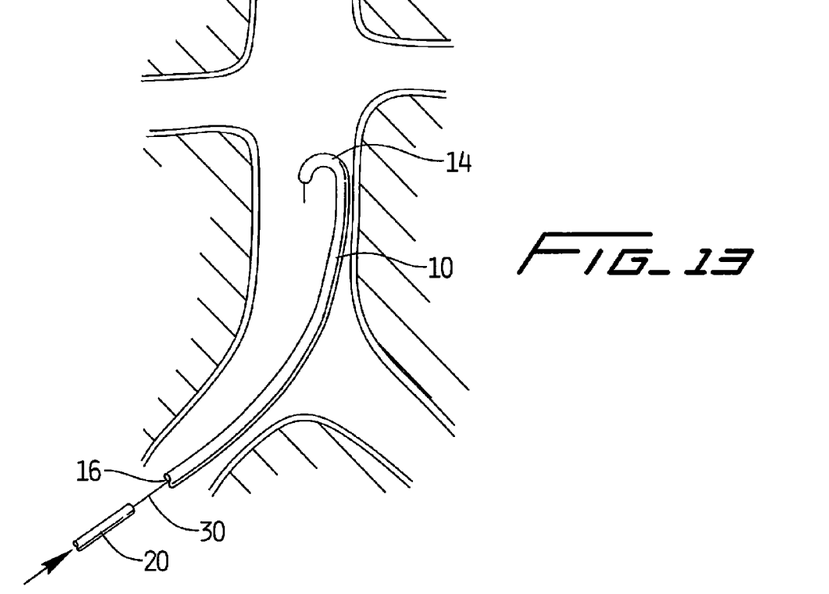
FIG. 13 illustrates reinsertion of the dilator into the retrieval catheter.
Figure 14:
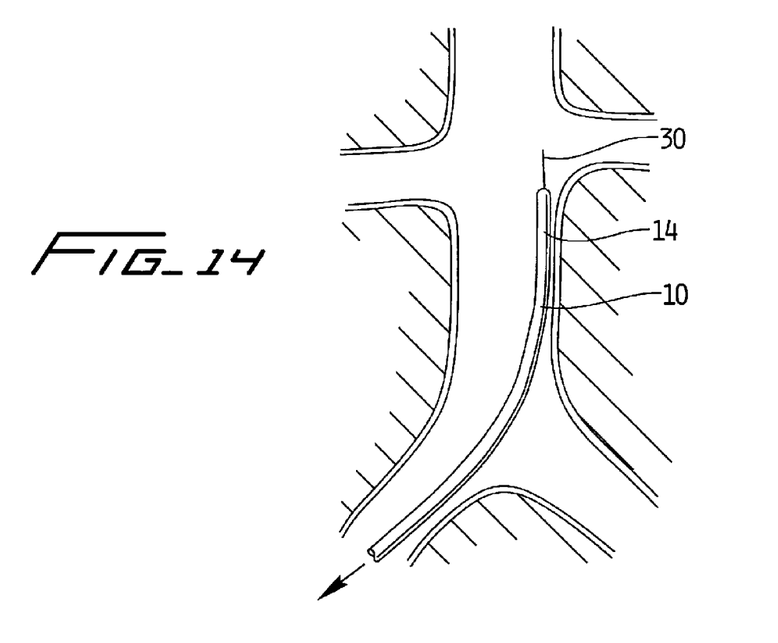
FIG. 14 illustrates removal of the catheter after advancement of the dilator to the distal tip to straighten the tip.

Once the filter retention hooks 58 are disengaged from the vessel wall, the snare catheter 40 is withdrawn, pulling the filter 50 into the retrieval catheter 10 as shown in FIG. 12. The snare catheter 40 and filter 50 are then removed through the proximal end of the catheter 10. Next, the dilator 20, preferably with guidewire 30, is reinserted through the catheter lumen 16 (FIG. 13) to straighten the distal tip 14 (or move it to more straightened position). The retrieval catheter 10, with the straightened tip, along with the dilator 20 and guidewire 30, are then withdrawn from the body in the direction of the arrow of FIG. 14.

Figures 17A, 17B:
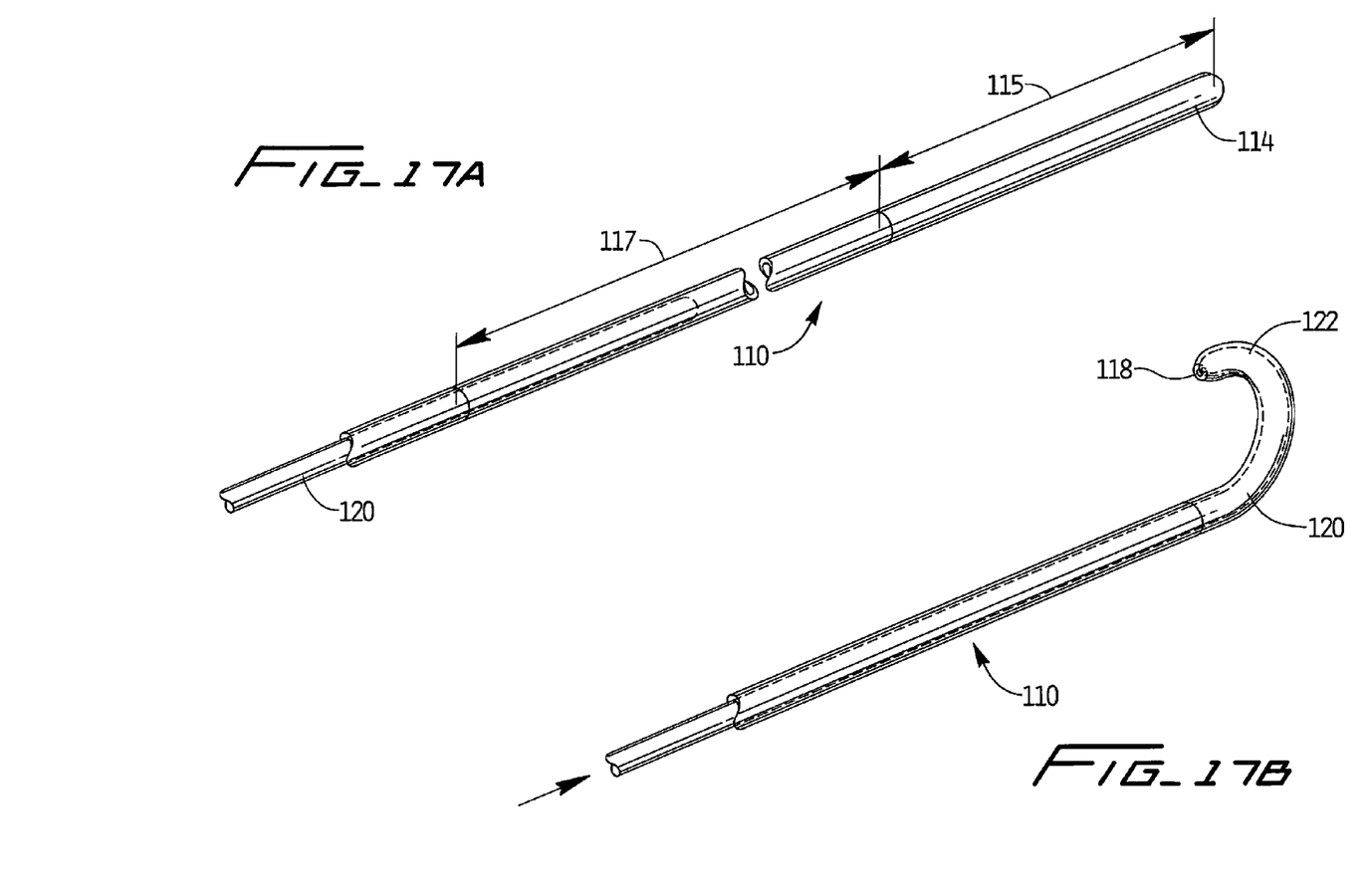
FIG. 17A is a broken perspective view of a retrieval catheter with a straight tip and showing a dilator being inserted therein.
FIG. 17B is a broken perspective view of the retrieval catheter of FIG. 17A with the dilator fully inserted to move the catheter tip to the curved position.

FIGS. 17A and 17B illustrate an alternate retrieval catheter. Retrieval catheter or sheath 110 has a substantially straight tip 114 and distal opening 118. The tip portion 115 of catheter 110 has a first hardness and the intermediate portion 117 (or portion proximal of tip portion 115) has a second hardness greater than the first hardness. A dilator or stylet 120 has a curved tip 122. The dilator 120 has a third hardness greater than the first hardness of the tip portion 115 but less than the second hardness of the intermediate portion 117. When the dilator 120 is inserted in the catheter 110 and the tip 122 is in the intermediate portion 117, the tip is restrained in a more straightened position due to the greater hardness of portion 117. When the dilator 120 is further inserted so the tip 122 is in the tip portion 115, it is enabled to return to its normally curved position since its hardness is greater than that of tip portion 115, thereby forcing the distal tip 114 of retrieval catheter 110 into a more curved position as shown in FIG. 17B.

Thus, in use, after insertion of the guidewire as described above, retrieval catheter 110, with dilator 120 positioned partially therein, is inserted through the femoral vein "f" and advanced through the iliac arteries into the inferior vena cava. Retrieval catheter 110 and dilator 120 are inserted over the guidewire past the caudal end 52 of the filter 50 and beyond the cranial end 54. (Alternatively, the dilator 120 can be inserted into catheter 110 after the catheter is inserted).

Dilator 120 is then fully inserted into the catheter 110 (and the guidewire withdrawn either prior to or after full insertion) to force the distal tip 114 of catheter 110 to its curved configuration. In this more curved configuration, the distal opening 118 of catheter 110 faces the cranial end of the filter and preferably is maneuvered so opening 18 is above the hook 56 of filter 50.

Snare catheter 40 is inserted through the lumen of the dilator 120 and extends around curved tip 122 of dilator 120 and curved distal tip 114 of catheter 110, exiting the distal opening of the dilator and the distal opening 118 of the catheter 110.

The snare 42 is placed around hook 56 of filter 50, and then tightened as described above. Once tightened, the catheter 10 is preferably moved distally, also as described above, to disengage the filter retention hooks 58 from the vessel wall. After the filter 50 is withdrawn, the dilator 120 is retracted to straighten the tip of catheter 110.

Figure 15A:
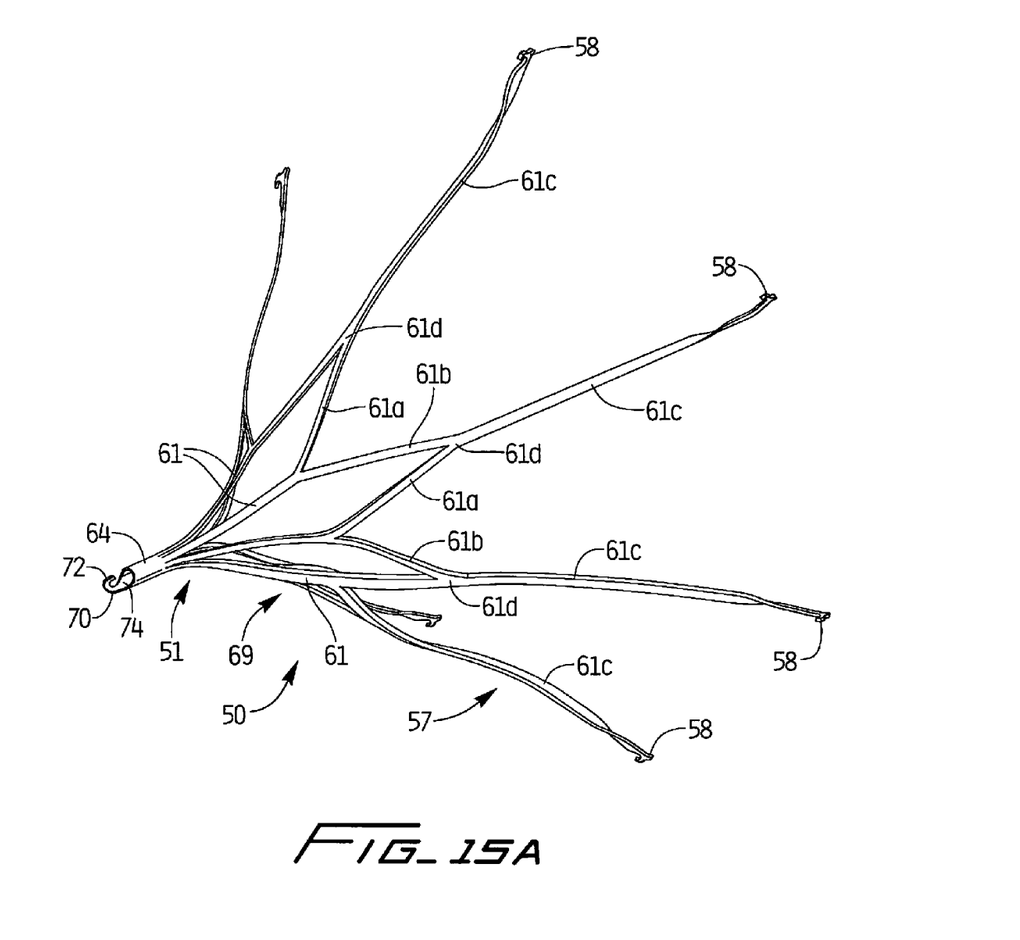
FIG. 15A is a perspective view of one embodiment of a vein filter that can be removed using the retrieval catheter.

FIG. 15 shows an example of a filter that could be withdrawn using the retrieval method of the present invention. The filter 50 is shown in the expanded placement configuration. It should be appreciated that other filters, including those described in the '429 application, could be retrieved using the femoral approach method described herein. The filter 50 (and other filters described therein) can be inserted through the jugular vein in the neck of the patient or through the femoral vein in the leg of the patient or the arm. The filters can also be placed in the superior vena cava.

Filter 50 is preferably made from a shape memory nitinol tube and has a flared region 57 and a converging region 51 at the filtering region 59.

Figure 15B:
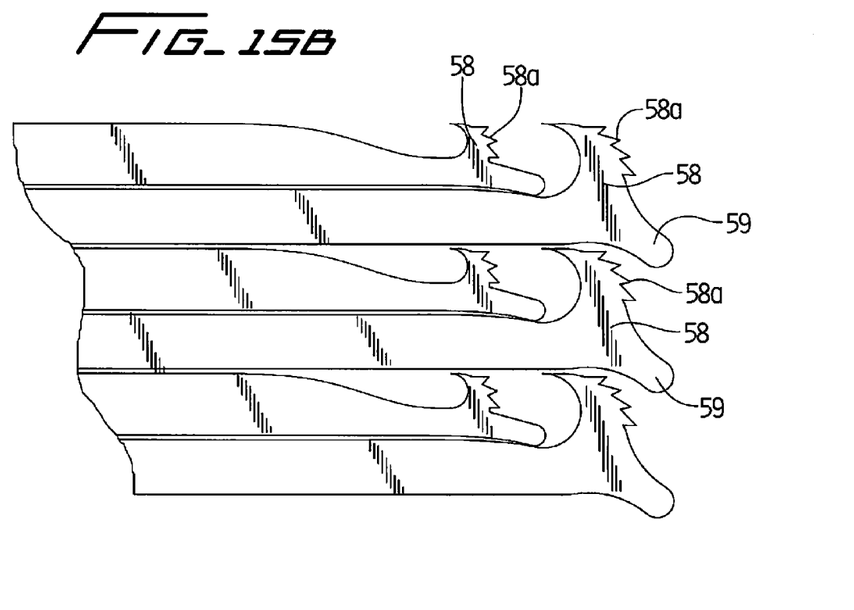
FIG. 15B is an enlarged developed view of the retention hooks of the filter of FIG. 15A.

Filtering region 69 has six struts 61 (only some of which are labeled for clarity) curving outwardly from tubular portion 64. Each filter strut or strut portion 61 extends radially from tubular portion 64 and divides into two connecting filter struts or strut portions 61a, 61b (preferably of equal width) that angle way from each other (in different directions) to extend to the connecting strut portion of an adjacent strut 61. After convergence of strut portions 61a, 61b at joining region 61d, it transitions into elongated mounting strut portions 61c which form flared mounting or anchoring region 57. The struts 61 terminate in hooks 58, of two different sizes as described in the '429 application. Hooks 58 include a series of teeth 58a (FIG. 15B) to engage the vessel wall to provide additional retention to prevent movement of the implanted filter in the caudal direction. A heel 59 extends past the hook to function as a stop to prevent the filter strut portions from going through the vessel wall.

The tubular portion 64 is preferably in the form of a retrieval hook as described in the '429 application. Hook 56 has a curved hook 72 at the proximal most end which is configured to receive a retrieval snare or other retrieval device. A portion of the wall of the hook 56 is cut out to expose the annular interior surface 74. The interior surface 74 accommodates a portion of a tubular snare sheath. That is, the outer wall of the snare sheath (tube) can partially fit within the cut out region. This enhances removal as the snare pulls the filter hook into collinear arrangement with the sheath tube.

Engagement of the retrieval hook 56 and its retraction into the snare sheath or tube, including the collinear arrangement are described in detail and shown in FIGS. 13H-13N of the '429 application. When the filter 50 is pulled into the retrieval sheath 10 it is collapsed for removal.

Figure 16:
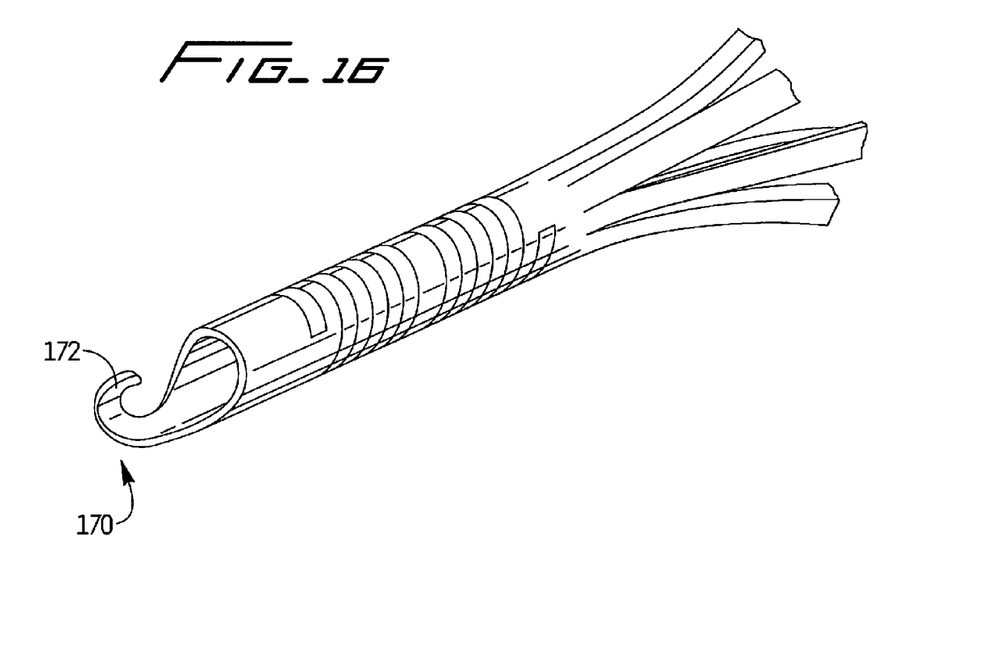
FIG. 16 is a perspective view of an alternate embodiment of a retrieval hook of a filter.
Figure 18:
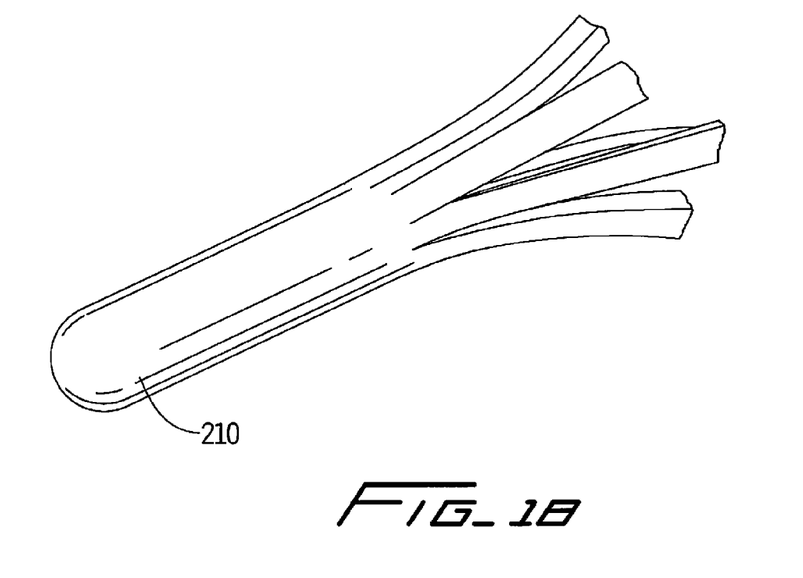
FIG. 18 is a perspective view of a cranial end of a filter have a dome shaped end.
Figure 19:
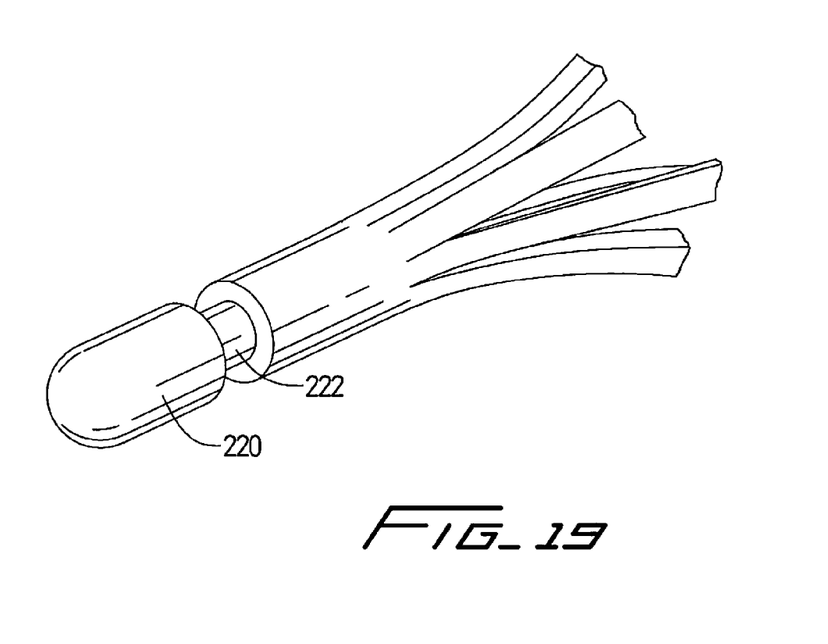
FIG. 19 is a perspective view of a cranial end of a filter having a dome shaped end with a notch formed therein.

FIG. 16 shows an alternate embodiment of a retrieval hook 170 having a longer hook 172 to increase the snare engagement area and provide a more closed area to retain the snare. FIGS. 18 and 19 illustrate alternative cranial ends of the filter which can be achieved using the method of the present invention. In FIG. 18, a rounded dome-shaped tip 210 can be engaged by a grasping device to retrieve the filter. The grasping device can be inserted around the curved catheter tip in the same manner as described above for the snare retrieval device. In FIG. 19, a notch 222 is formed in dome-shaped tip 220 to receive a retrieval snare or other grasping device inserted through the curved retrieval catheter (sheath) tip.

To facilitate removal of the filter from the vessel, cold saline can be injected onto the implanted filter to change the temperature of the filter to move it to a relatively softer condition to facilitate the filter being drawn in to the retrieval sheath. That is, injection of cold saline will cause the filter to approach its softer martensitic state, bringing the filter to a more flexible condition. The flexible condition facilitates the collapse and withdrawal of the filter into the retrieval sheath by decreasing the frictional contact between the filter and the inner surface of the retrieval sheath.

While the above description contains many specifics, those specifics should not be construed as limitations on the scope of the disclosure, but merely as exemplifications of preferred embodiments thereof. Those skilled in the art will envision many other possible variations that are within the scope and spirit of the disclosure as defined by the claims appended hereto.

What is claimed is:

1. A method of removing an implanted vessel filter by a femoral approach comprising the steps of:
   providing a catheter with a tip;
   inserting a curved device into the catheter to a position proximal of the tip;
   advancing the catheter tip through the femoral vein and past a cranial end of the implanted filter;
   inserting the curved device into the catheter tip to move the catheter tip from a first more straightened position to a second more curved position; and
   inserting a filter grasping device through the curved device, catheter and curved catheter tip to exit a distal portion of the catheter to grasp the filter, wherein the tip of the catheter terminates in an opening and the step of inserting the curved device moves the opening to face a proximal portion of the catheter and the cranial end of the filter.

2. The method of claim 1, wherein the catheter has a first hardness at an intermediate portion and a second hardness less than the first hardness at the tip such that in the step of inserting the curved device, the first hardness maintains the curved device in the first more straightened position and the second hardness allows the curved device to move to the second more curved position to thereby move the catheter tip to the second more curved position.

3. The method of claim 2, wherein the step of inserting a curved device into the catheter occurs subsequent to the step of advancing the catheter tip through the femoral vein.

4. The method of claim 2, wherein the curved device has a third hardness greater than the second hardness and less than the first hardness.

5. The method of claim 1, further comprising the step of pulling the filter into a lumen of the curved device after grasping of the filter.

6. The method of claim 1, wherein the step of advancing the catheter tip includes the step of advancing the catheter and curved device over a guidewire.

7. The method of claim 1, further comprising the step of withdrawing the filter and grasping device through the catheter, wherein subsequent to the step of withdrawing the filter, the method includes the step of withdrawing the curved device from the catheter tip to move the catheter tip to the first more straightened position.

8. The method of claim 1, wherein the step of inserting the filter grasping device comprises the step of inserting the filter grasping device through a proximal portion of the catheter and through the tip to exit the opening in the catheter tip.

* * * * *